United States Patent [19]

Zalkin et al.

[11] 4,215,681

[45] Aug. 5, 1980

[54] RESPIRATOR FOR THE TREATMENT OF PERSONS SUFFERING FROM RESPIRATORY INSUFFICIENCIES

[75] Inventors: Daniel Zalkin, Clichy; Jean-Pierre Maillot, Paris, both of France

[73] Assignee: Assistance Technique Medicale Serdahl, S.A., Maurepas, France

[21] Appl. No.: 875,758

[22] Filed: Feb. 7, 1978

Related U.S. Application Data

[63] Continuation of Ser. No. 711,515, Aug. 4, 1976, abandoned.

[30] Foreign Application Priority Data

Aug. 7, 1975 [FR] France .................................. 75 24621

[51] Int. Cl.$^2$ ............................................. A61M 16/00
[52] U.S. Cl. ............................ 128/204.21; 128/205.18
[58] Field of Search ............... 128/145.8, 145.6, 145.5, 128/142.2, 188, 203, 142 R, DIG. 17; 310/23, 27

[56] References Cited

U.S. PATENT DOCUMENTS

| | | | |
|---|---|---|---|
| 2,830,580 | 4/1958 | Saklad et al. | 128/DIG. 17 |
| 3,101,708 | 8/1963 | Perry et al. | 128/145.5 |
| 3,808,676 | 5/1974 | Schrock et al. | 310/23 |
| 3,863,082 | 1/1975 | Gillott et al. | 128/145.6 |
| 3,910,270 | 10/1975 | Stewart | 128/145.8 |
| 4,001,700 | 1/1977 | Cook et al. | 128/DIG. 17 |

*Primary Examiner*—Henry J. Recla
*Attorney, Agent, or Firm*—Robert E. Burns; Emmanuel J. Lobato; Bruce L. Adams

[57] ABSTRACT

A respirator is provided for the treatment, particularly in the home, of persons suffering from respiratory insufficiencies. The respirator comprises a reciprocating linear electric motor compressor having a gas intake orifice connected to atmosphere for example, a compressed gas discharge orifice connected to a respiratory mask, a piston, a spring acting on the piston, and an electromagnet for moving the piston against the action of the spring to supply compressed gas to the mask via the discharge orifice. A thyristor pulse generator is controlled by a clock to provide pulses to the electromagnet to define the insufflation time. The compressor operates only during the insufflation time.

8 Claims, 2 Drawing Figures

RESPIRATOR FOR THE TREATMENT OF PERSONS SUFFERING FROM RESPIRATORY INSUFFICIENCIES

This is a continuation of application Ser. No. 711,515, filed Aug. 4, 1976 now abandoned.

BACKGROUND OF THE INVENTION

The present invention relates to a respirator for the treatment of persons suffering from respiratory insufficiencies, which can be used more particularly in the home.

The regulations relating to the ratification of respirators prohibit the use of compressed gas as a source of energy, when these respirators are used to treat a person suffering from respiratory insufficiencies in the home. Consequently, known apparatus of this type are generally electrical appliances using connecting rod and crank systems with compressors having a rotary or alternating movement, which are used with a device for dividing up the time to produce insufflation and expiration phases for the patient, electronically or pneumatically.

Consequently, these apparatus have the drawback of having a large number of moving parts and of operating continuously throughout the treatment period.

The present invention intends to remedy this drawback by providing a respirator of particularly simple design, whereof the number of moving mechanical parts is very low and the actual operating time is reduced, which makes it possible to increase the reliability considerably.

SUMMARY OF THE INVENTION

To this end, this respirator for the treatment of persons suffering from respiratory insufficiencies, in particular in the home, comprising an alternating movement compressor, whose intake orifice is connected to a source of gas, in particular the atmosphere and possibly a source of additional oxygen and whose discharge orifice is connected to a respiratory mask, is characterised in that the compressor is of the type having a linear electric motor comprising a piston attracted by an electromagnet and repelled by a spring and in that the winding of the electromagnet is connected to a pulse generator comprising a thyristor controlled by a clock determining the insufflation and expiration times, such that this generator supplies excitation pulses, applied to the electromagnet of the compressor, solely duling the period of insufflation and due to this the compressor operates solely during this period.

The respirator according to the invention has the advantage of being more economical due to less wear of the moving parts and consequently has a longer life expectancy. Its safety is increased, it makes it possible to eliminate the use of an electric valve, its consumption of energy is reduced and its circuits are very simplified.

BRIEF DESCRIPTION OF THE DRAWINGS

One embodiment of the present invention will be described hereafter, as a non-limiting example, with reference to the accompanying drawings in which.

DESCRIPTION OF THE PREFERRED EMBODIMENTS

Figure 1:
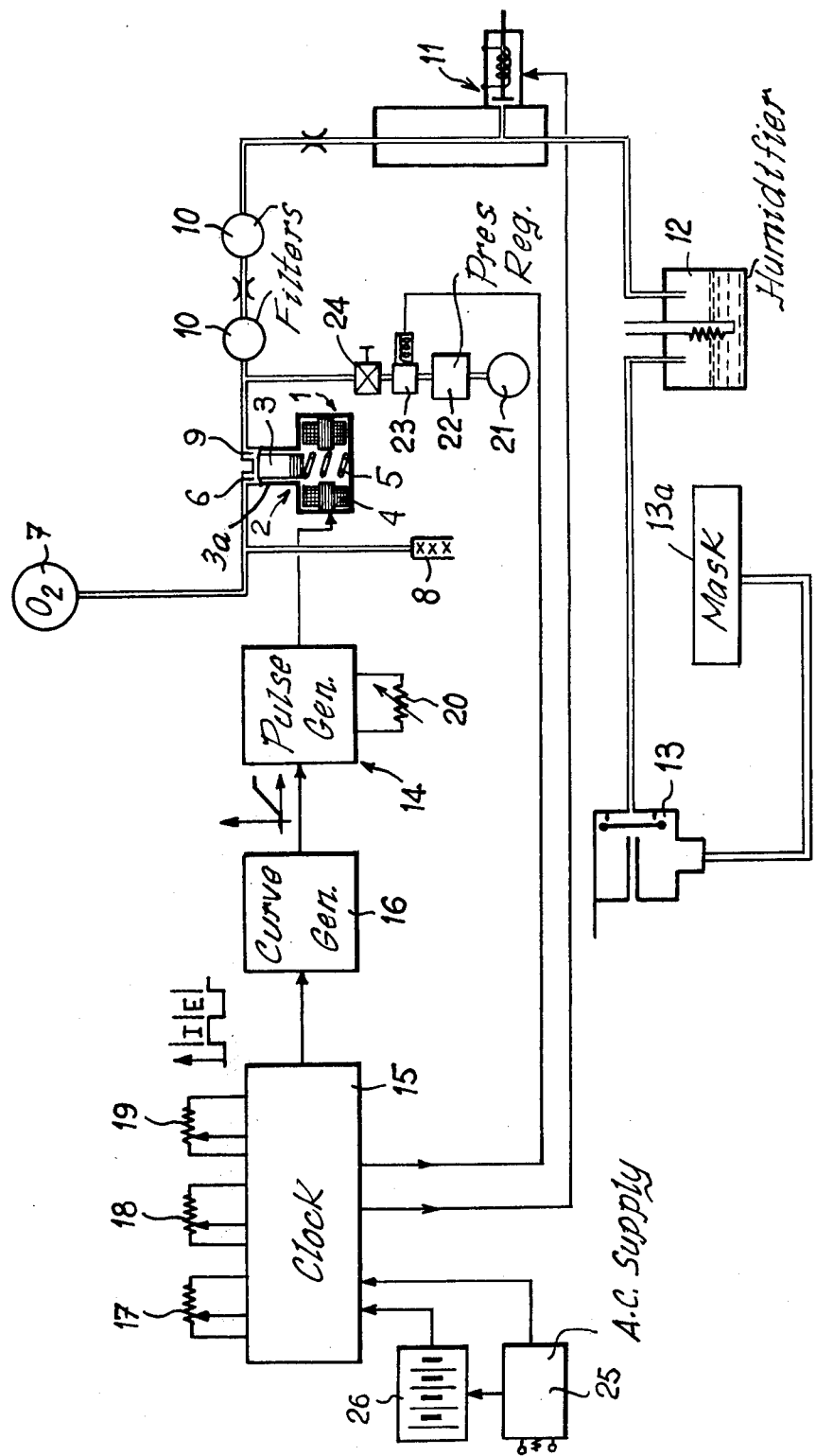
FIG. 1 is a synoptic diagram of the respirator comprising a compressor according to the invention.

The respirator according to the invention essentially comprises a compressor 1 of the type having a linear electric motor 2. This motor comprises a moving piston 3 slidably mounted in a cylinder 3a attracted by an electromagnet 4 and repelled by a spring 5. The intake orifice 6 of the compressor is connected to a source of gas which may be an oxygen tank 7 or an air inlet 8. The discharge orifice 9 of the compressor is connected to a respiratory mask 13a placed on the patient, through the intermediary of filters 10, an electric valve 11 for connection to the atmosphere, a humidifier 12 and an expiratory valve 13 connected to the respiratory mask proper.

The motor 2 of the compressor 1 is connected to a pulse generator 14 comprising a semiconductor of the type, which is in turn connected to a clock 15 directly or through the intermediary of a curve generator 16, as shown in FIG. 1. The clock 15, of any appropriate type, produces a periodic signal at its output, a first phase of which signal corresponds to the insufflation time I and the second phase to the expiration time E. The durations of these phases are respectively determined by means of associated control members, such as potentiometers, namely a potentiometer 17 for controlling the insufflation phase I and a potentiometer 18 for controlling the expiration phase E. A third potentiometer 19 may also be provided for controlling the duration of a pressure stage immediately following the insufflation stage I. To this end, the clock is also connected to the electric valve 11.

The operation of the respirator according to the invention will now be described also with reference to the diagram of FIG. 2.

At its output, the clock 15 emits a periodic square wave signal whose peak I, the duration of which can be adjusted by means of the potentiometer 17, determines the insufflation time and whose trough E, the duration of which may be adjusted by means of the potentiometer 18, determines the expiration time.

This signal is transmitted to the curve and wave generator 16 which produces a signal having a sloping ascending side, at its output, when it is desired to obtain a progressive rise and increase in the output Q provided by the compressor. This signal is sent to the pulse generator 14 comprising a thyristor, which may be of any known type and which essentially comprises a current generator, a relaxer and an amplifier. At its output, this pulse generator supplies control pulses, at a current supply or mains frequency such as 50 Hz, these pulses being cut into the basic sinusoidal signal of the supply frequency 50 Hz, in order to have a width depending on the desired output Q. This output may be controlled manually by means of a potentiometer 20 connected to the generator 14 and varying the angle of opening of the thyristor.

Figure 2:
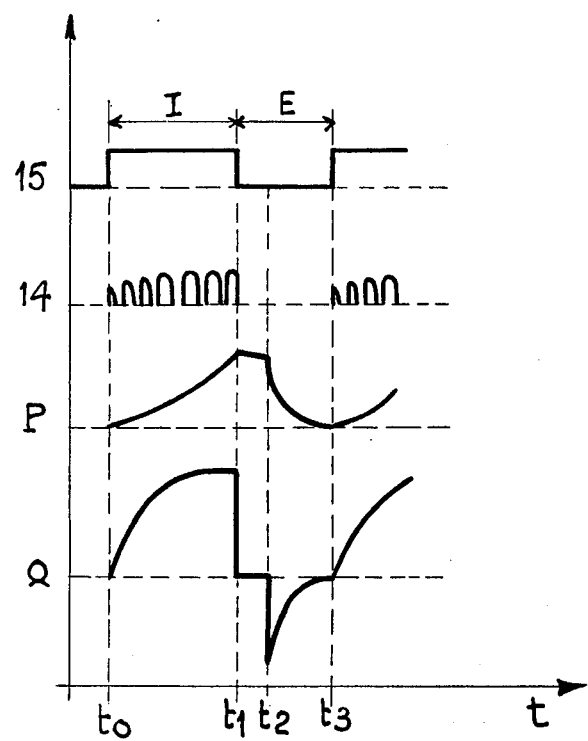
FIG. 2 is a diagram illustrating the operation of the respirator.

As can be seen from FIG. 2, the generator 14 emits control pulses only when the insufflation signal I is present. These pulses are applied to the winding of the electromagnetic 4 of the motor 2 of the compressor, such that the latter operates at the supply frequency rate of 50 Hz solely during each insufflation stage. It will be understood that the volume of displacement of the piston 3 in the cylinder 3a is small in relation to the average tidal volume of a patient. During the following expiration stage, it remains inoperative.

The curves P and Q of FIG. 2 respectively show the variation of pressure and output of the compressor during a complete cycle of the respirator according to the invention. From the time $t_0$ of the beginning of a cycle until the time $t_1$ marking the end of the insufflation stage, the pressure rises progressively and the output increases relatively steeply at the beginning to remain constant throughout the later part of the insufflation stage. To this end, it will be seen that the pulses emitted by the generator 14 have a width increasing progressively at the beginning of this stage, then constant at the end.

If desired, as seen previously, it is possible to provide a pressure stage at the end of the insufflation stage. To this end, the clock 15 controls the opening of the electric valve 11, only at the instant $t_2$, after the instant $t_1$. Due to this, when the output Q drops to zero at the instant $t_1$, the pressure P remains virtually at its maximum value during the interval of time $t_1$–$t_2$, after which it drops quite quickly when the electric valve 11 is opened at the time $t_2$. At this time, the patient may breathe out through the expiratory valve 13, which is opened to both the mask and the atmosphere by a negative output Q as shown in FIG. 1.

This expiration phase terminates at the instant $t_3$ where a new cycle begins.

The respirator according to the invention can be provided with conventional means making it possible to ensure its operation with complete safety. For this purpose a compressed air reservoir 21 can be connected to the outlet of the compressor 1, by means of a pressure regulator 22, an electric valve 23 connected to the clock 15 and a valve 24. Another emergency device is provided for the supply of electric current to the clock 15. The latter is normally supplied with current by a supply unit 25 connected to the mains. Nevertheless, in order to be able to obviate a mains failure, an emergency supply is provided, in the form of a battery 26 which is permanently charged by the supply unit 25, and which can be suitably used to supply the clock 15, if there is a mains failure.

Should there be an accidental breakdown of the compressor 1 or mains failure, it is thus possible to use the emergency air reservoir 21, the clock 15 opening and closing the electric valve 23 periodically, in order to supply the patient with compressed air, directly from the emergency reservoir 21. In fact, it is difficult to supply the compressor from the battery 26, in the case of a mains failure. This supply would require the provision of a conventional converter and a very large battery. This drawback is remedied by means of the compressed air reservoir 21.

What is claimed is:

1. A respirator for persons suffering from respiratory insufficiencies comprising:
   a respiratory mask,
   a recipricatory compressor comprising a cylinder having a gas intake orifice and a compressed gas discharge orifice, a piston slidable in said cylinder, spring means acting on said piston to slidably move it in a direction toward said discharge orifice, electromagnet means for moving said piston in a direction away from said discharge orifice when said electromagnetic means is energized, the volume of displacement of said piston in said cylinder being substantially less than the average tidal volume of a patient,
   means connecting said intake orifice with a gas supply and means connecting said discharge orifice with said respiratory mask,
   means for energizing said electromagnetic means comprising a supply unit connected to alternating current mains of standard frequency, pulse generating means for supplying to said electro-magnet periodic pulses having a frequency corresponding to said standard frequency when said pulse generating means is energized, and means connecting said pulse generating means with said supply unit comprising clock means for energizing said pulse generating means with alternating current of said standard frequency from said alternating current mains during spaced periods corresponding to insufflation periods and deenergizing said pulse generating means during intervening periods corresponding to expiration periods,
   whereby said pulse generating means supplies pulses at said standard frequency to said electromagnetic means to produce reciprocation of said piston in said cylinder at said standard frequency to pump gas from said gas supply to said respiratory mask under pressure during said insufflation periods only, said electromagnetic means being deenergized and said piston being inoperative during intervening exhalation periods,
   control means for modifying said pulses supplied by said pulse generating means to said electromagnetic means by varying the width of said pulses and thereby controlling the output of said compressor, and
   valve means for venting said respiratory mask to the atmosphere to relieve said pressure during said exhalation periods.

2. A respirator according to claim 1, in which said valve means is electrically operated and is controlled by said clock means.

3. A respirator according to claim 2, in which said clock means controls said valve means to open a predetermined period of time after said electromagnetic means is deenergized at the end of an insufflation period to provide a delay interval in which pressure is maintained between the cessation of pumping and the venting of said respiratory mask to the atmosphere.

4. A respirator according to claim 3, in which said clock means includes means for adjustably setting said insufflation period, said delay interval and said exhalation period.

5. A respirator according to claim 1, in which said means connecting the discharge orifice of said compressor with said respiratory mask includes means for attenuating any pulses generated by said reciprocatory compressor.

6. A respirator according to claim 1, in which said control means comprises a potentiometer.

7. A respirator according to claim 1, in which said control means comprises a programmable curve generator controlling said pulse generating means.

8. A respirator according to claim 1, comprising safety means including a reserve compressed gas storage means and means connecting said storage means with said respiratory, including an electric valve controlled by said clock means to open during insufflation periods to supply gas to said respiration mask in the event said compressor does not operate.

* * * * *